(12) United States Patent
Pan et al.

(10) Patent No.: US 7,803,115 B2
(45) Date of Patent: Sep. 28, 2010

(54) METHOD AND APPARATUS FOR MULTIPLE TRANSMIT CONTRAST IMAGING

(75) Inventors: Lihong Pan, Brookfield, WI (US); Michael Joseph Washburn, Brookfield, WI (US); Kirstin Nora LaConte, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 600 days.

(21) Appl. No.: 11/879,449

(22) Filed: Jul. 16, 2007

(65) Prior Publication Data

US 2009/0024036 A1 Jan. 22, 2009

(51) Int. Cl.
*A61B 8/00* (2006.01)
*A61B 8/14* (2006.01)

(52) U.S. Cl. .................. 600/447; 600/458
(58) Field of Classification Search ............. 600/437, 600/440–447, 458
See application file for complete search history.

(56) References Cited

U.S. PATENT DOCUMENTS 6,494,841 B1 12/2002 Thomas et al.
6,602,195 B1 8/2003 Krishnan et al.

*Primary Examiner*—Eric F Winakur
*Assistant Examiner*—Michael T Rozanski
(74) *Attorney, Agent, or Firm*—Dean D. Small; Small Patent Law Group

(57) ABSTRACT

A method for measuring a non-linear response from a target using an imaging apparatus includes transmitting a signal towards a region of interest from a transducer at a first amplitude and measuring a first response thereto, and transmitting, from the transducer towards the region of interest, at least one additional signal of the same phase as the first amplitude signal but at one or more different, lower amplitudes and measuring at least one additional response thereto. A difference of a function of the measured additional response or responses from the first response is determined, thereby obtaining a non-linear response of the object of interest, and a representation of the non-linear response is displayed.

20 Claims, 11 Drawing Sheets

METHOD AND APPARATUS FOR MULTIPLE TRANSMIT CONTRAST IMAGING

BACKGROUND OF THE INVENTION

This invention relates generally to diagnostic ultrasound medical imaging, and more particularly, to methods and apparatus for detecting nonlinear echoes from contrast agents.

Contrast agents can be used in diagnostic medical imaging to aid in the detection of diseased tissues. In some detection methods, the nonlinear response of the contrast agent relative to normal tissue is used to distinguish between ultrasound echoes resulting from the presence of contrast agent from those of normal tissue.

Ultrasound contrast imaging methods are known that use multiple pulses where at least two pulses are of different amplitude and at least two pulses are of different phases. The multiple pulse techniques suppress the linear echo and preserve the nonlinear echoes from contrast agents. These techniques, however, work well only when the transmit pulses that have a 180 degree phase shift with respect to each other are exactly symmetric (i.e., the sum of the pulses with 180 degree phase shift with respect to each other is zero).

BRIEF DESCRIPTION OF THE INVENTION

In accordance with one embodiment of the present invention, a method is provided for measuring a non-linear response from a target using an imaging apparatus. The method includes transmitting a signal towards a region of interest from a transducer at a first amplitude and measuring a first response thereto, and transmitting, from the transducer towards the region of interest, at least one additional signal of the same phase as the first amplitude signal but at one or more different, lower amplitudes and measuring at least one additional response thereto. A difference of a function of the measured additional response or responses from the first response is determined, thereby obtaining a non-linear response of the object of interest, and a representation of the non-linear response is displayed.

In another embodiment of the present invention, a diagnostic imaging apparatus for measuring a non-linear response from a target is provided. The apparatus includes a transmitter, a transducer having a plurality N of excitable transducer elements excitable by the transmitter, a beamformer configured to focus a beam from the transducer at a position to transmit acoustic energy and to receive echo return signals from the transducer elements, a summing/differencing module responsive to the beamformer and configured to determine a non-linear response, and a display configured to display a representation of the determined non-linear response. The apparatus is configured to transmit a signal towards a region of interest from the transducer at a first amplitude and measure a first response thereto, and transmit, from the transducer towards the region of interest, at least one additional signal of the same phase as the first amplitude signal but at one or more lesser amplitudes and measure at least one additional response thereto. The apparatus is further configured to determine a difference of a function of said measured at least one additional response from the first response to thereby determine a non-linear response of the object of interest, and to display a representation of the non-linear response on the display.

In yet another embodiment of the present invention, the diagnostic imaging apparatus is an ultrasound imaging apparatus.

DETAILED DESCRIPTION OF THE INVENTION

Figure 1:
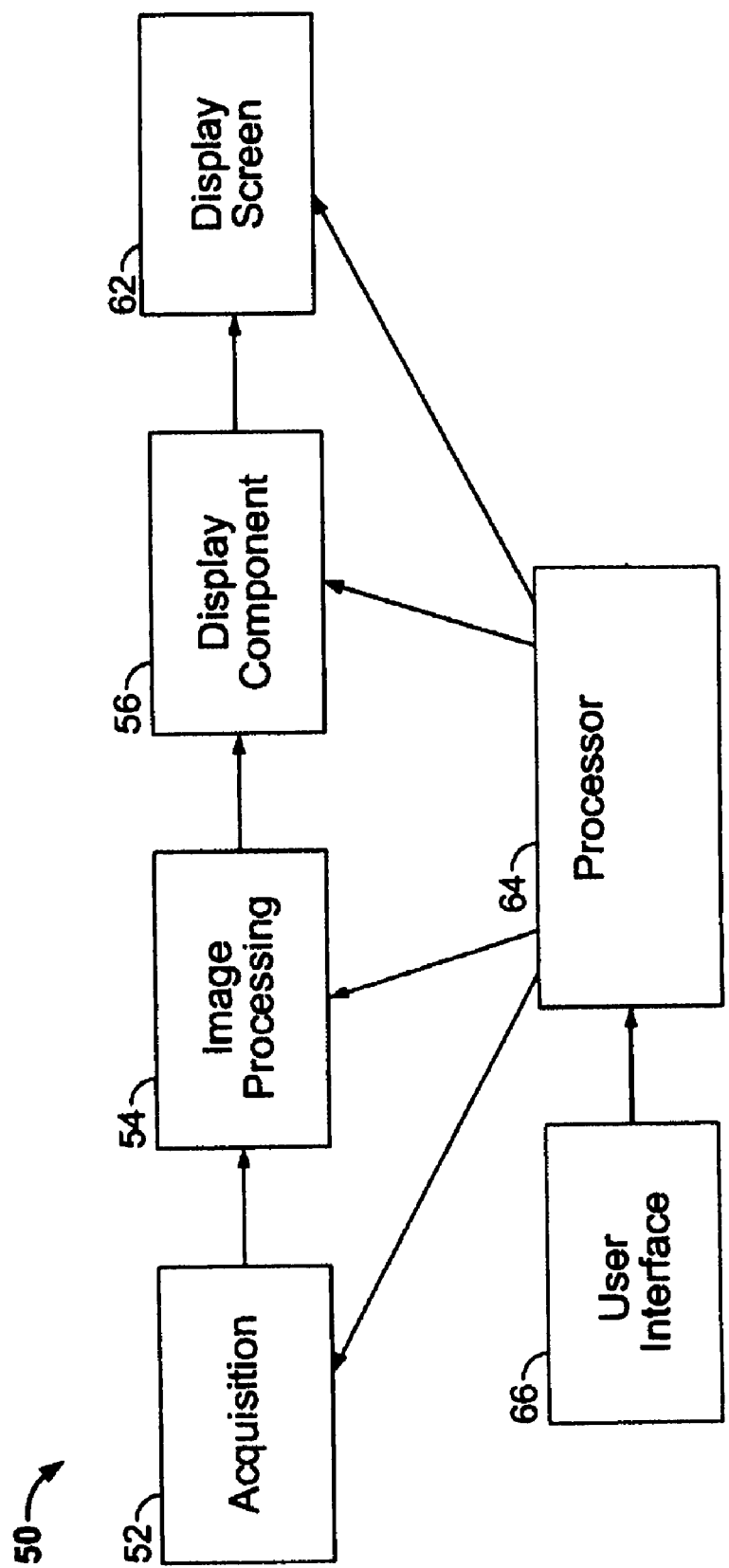
FIG. 1 is a block diagram of a diagnostic imaging apparatus constructed in accordance with an embodiment of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments of the invention provide a diagnostic imaging apparatus 50 as shown in FIG. 1 that automatically optimizes viewing of images. Diagnostic imaging apparatus 50 may be any type of system, for example, different types of medical imaging systems, such as an ultrasound imaging apparatus or a multi-modality imaging apparatus, among others, in which the phase of the transmitted signal is controlled and non-linearities with respect to the signal in an object of interest are significant. The various embodiment are not limited to medical imaging systems or imaging systems for imaging human subjects, but may include veterinary or non-medical systems for imaging non-human objects and systems for performing non-destructive imaging or testing, security imaging (e.g., airport security screening), etc.

Diagnostic imaging apparatus 50 generally includes an acquisition component 52 configured to acquire image data (e.g., ultrasound image data). Acquisition component 52 may be, for example, a probe, scanner or other similar device for scanning an object or volume of interest. Acquisition component 52 is connected to an image processing component 54. Image processing component 54 is any type of image processor capable of processing the acquired image data and is connected to a display component 56. Display component 56 configures or formats the processed image data for display on a display screen 62. The display screen 62 may be any type of screen capable of displaying images, graphics, text, etc. For example, the display screen 62 may be a cathode ray tube (CRT) screen, a liquid crystal display (LCD) screen or a plasma screen, among others.

A processor 64 (e.g., computer) or other processing unit controls the various operations within diagnostic imaging apparatus 50. For example, processor 64 may receive user inputs from a user interface 66 and display requested image data or adjust the settings for the displayed image data.

Figure 2:
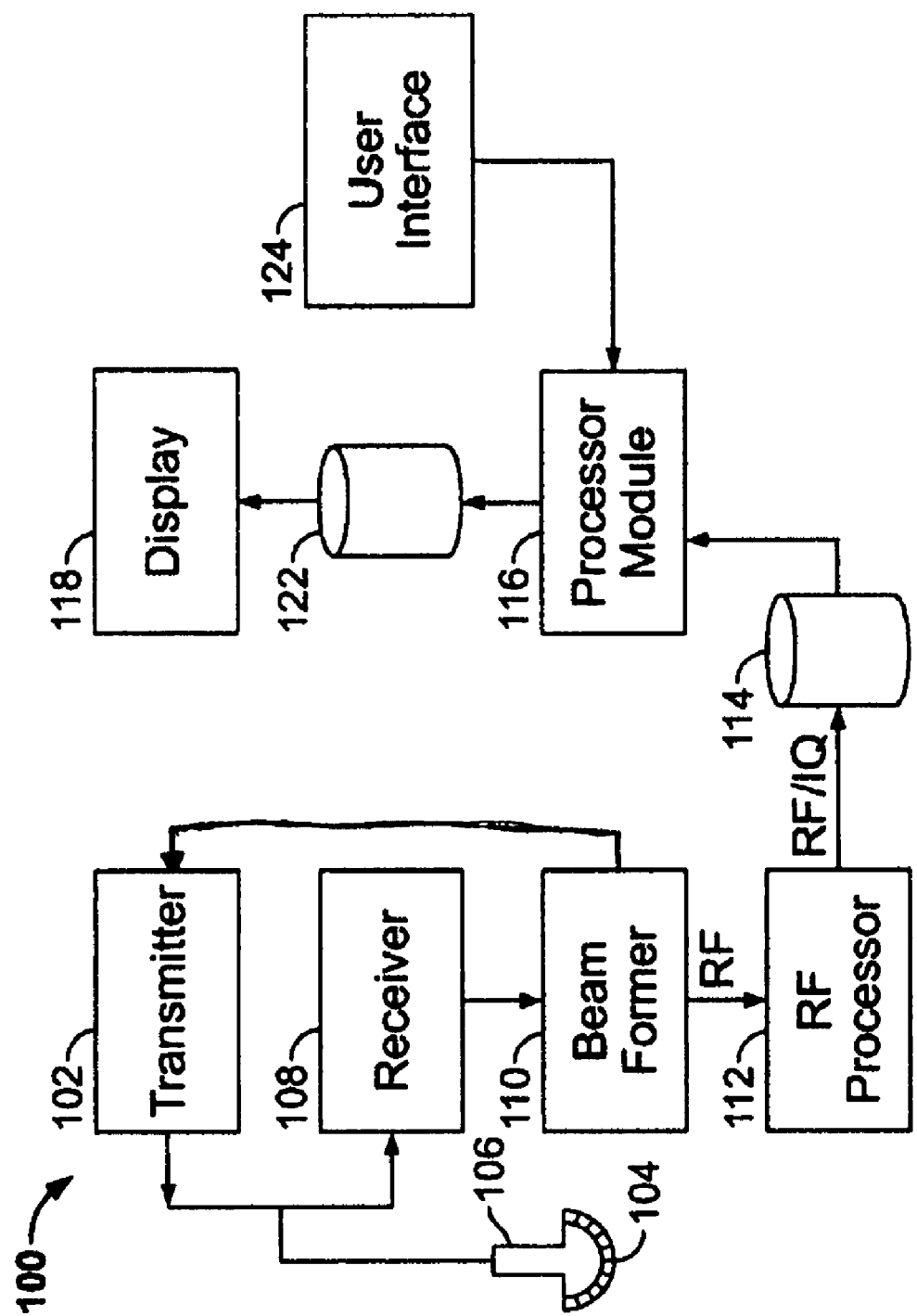
FIG. 2 is a block diagram of an ultrasound imaging apparatus constructed in accordance with an embodiment of the invention.

Diagnostic imaging apparatus 50 may be, for example, an ultrasound imaging apparatus 100 shown in FIG. 2. Ultrasound imaging apparatus 100 includes a transmitter 102 that drives an array of elements 104 (e.g., piezoelectric or other elements) within a transducer 106 to emit pulsed ultrasonic signals into a body. The transmit energy is focused at a given position through the control of a beamformer 110. It should be noted that at a given focus depth, the elements 104 that are excited may be less than the total number of elements 104 forming the array. For example, if the total number of elements 104 is N, then at a given focus depth, the full aperture $n \leq N$. A variety of geometries may be used. The ultrasonic signals are back-scattered from structures in the body, like blood cells or muscular tissue, to produce echoes that return to the elements 104. The echoes are received by a receiver 108. The received echoes are passed through the beamformer 110, which performs beamforming and outputs an RF signal. The RF signal then passes through an RF processor 112. Alternatively, RF processor 112 may include a complex demodulator (not shown) that demodulates the RF signal to form IQ data pairs representative of the echo signals. The RF or IQ signal data may then be routed directly to a memory 114 for storage.

Ultrasound imaging apparatus 100 also includes a processor module 116 to process the acquired ultrasound information (e.g., RF signal data or IQ data pairs) and prepare frames of ultrasound information for display on display 118. Processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and the processed and displayed in off-line operation.

Processor module 116 is connected to a user interface 124 that may control operation of processor module 116 as explained below in more detail. Display 118 includes one or more monitors that present patient information, including diagnostic ultrasound images to the user for diagnosis and analysis. One or both of memory 114 and memory 122 may store three-dimensional data sets of the ultrasound data, where such 3-D data sets are accessed to present two-dimensional (2D) and three-dimensional (3D) images. The images may be modified and the display settings of display 118 also manually adjusted using user interface 124.

Ultrasound imaging apparatus 100 may obtain volumetric data sets by various techniques (e.g., 3D scanning, real-time 3D imaging, volume scanning, 2D scanning with transducers having positioning sensors, freehand scanning using a Voxel correlation technique, 2D or matrix array transducers and the like). Transducer 106 is moved, such as along a linear or arcuate path, while scanning a region of interest (ROI). At each linear or arcuate position, transducer 106 obtains scan planes that are stored in memory 114.

Figure 3:
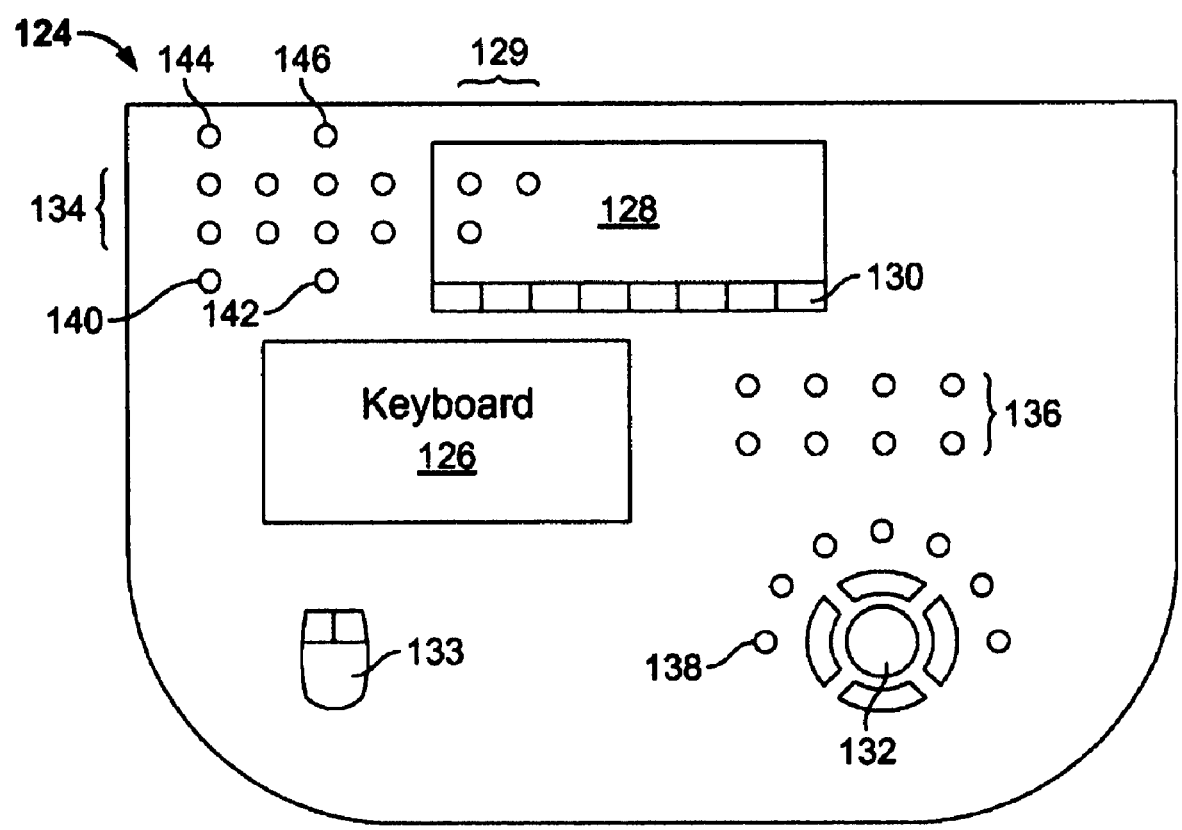
FIG. 3 is a top plan view of a user interface constructed in accordance with an embodiment of the invention.

FIG. 3 illustrates user interface 124 constructed in accordance with one embodiment of the invention. User interface 124 can include a keyboard 126, a mouse 133 (more commonly found in off-line imaging systems and workstations than in an ultrasound imaging apparatus), a touch screen 128, a series of soft keys 130 proximate touch screen 128, a trackball 132, view position buttons 134, mode buttons 136 and control or operation keys 138. Soft keys 130 are assigned different functions on touch screen 128 depending upon a selected examination mode, stage of examination and the like. Trackball 132 and keys 138 are used to control the display of images on display 118 and control various options, for example, zoom, rotate, viewing mode, examination mode, etc. For example, view position buttons 134 may change different views of the displayed image. Optionally, view position buttons 134 may be implemented as touch areas 129 on touch screen 128. As a further option, the size, position and orientation of the displayed image may be controlled partially or entirely by touch areas provided on touch screen 128 and/or by the soft keys 130.

User interface 124 also includes other controls, such as a save command/option 140 and a restore command/option 142 to save or restore certain image characteristics or changes to the displayed image. However, it should be noted that the various controls may be used to adjust or control different settings, display options, etc. For example, user interface 124 may include a brightness control button 144 that allows a user to manually adjust screen brightness and a contrast control button 146 that allows a user to manually adjust screen contrast.

Figure 4:
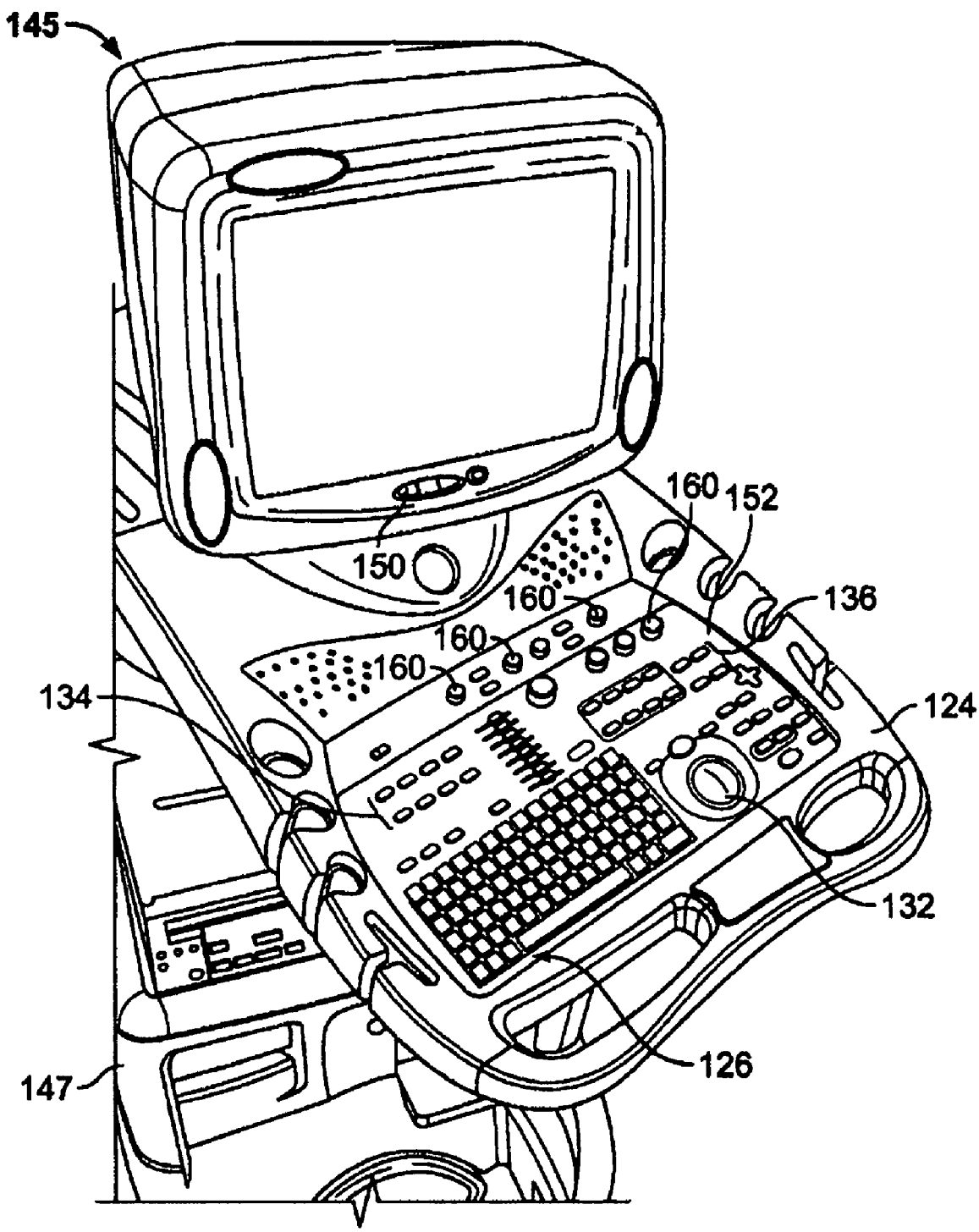
FIG. 4 is a perspective view of a portable medical imaging apparatus constructed in accordance with an embodiment of the invention.

Embodiments of the present invention may, for example, be implemented in a portable imaging apparatus 145 (e.g., portable ultrasound apparatus) provided on a movable base 147, as shown in FIG. 4. Manual screen adjustment controls 150 (e.g., brightness and contrast controls) are provided on display 118. It should be understood that display 118 may be separate or separable from user interface 124. User interface 124 may optionally be a touchscreen, allowing the user to select options by touching displayed graphics, icons, and the like.

User interface 124 of FIG. 4 also includes other optional control buttons 152 that may be used to control portable imaging apparatus 145 as desired or needed, and/or as typically provided. User interface 124 provides multiple interface options that the user may physically manipulate to interact with ultrasound data and other data that may be displayed, as well as to input information and set and change scanning parameters. The interface options may be used for specific inputs, programmable inputs, contextual inputs, and the like. Different types of physical controls are provided as different physical actions are more intuitive to the user for accomplishing specific system actions and thus achieving specific system responses.

For example, multi-function controls 160 are positioned proximate to display 118 and provide a plurality of different physical states. For example, a single multi-function control may provide movement functionality of a clockwise/counter-clockwise (CW/CCW) rotary, up/down toggle, left/right toggle, other positional toggle, and on/off or pushbutton, thus allowing a plurality of different states. Different combinations are possible and are not limited to those discussed herein. The multi-function controls 160 may be configured, for example, as joystick rotary controls.

Figure 5:
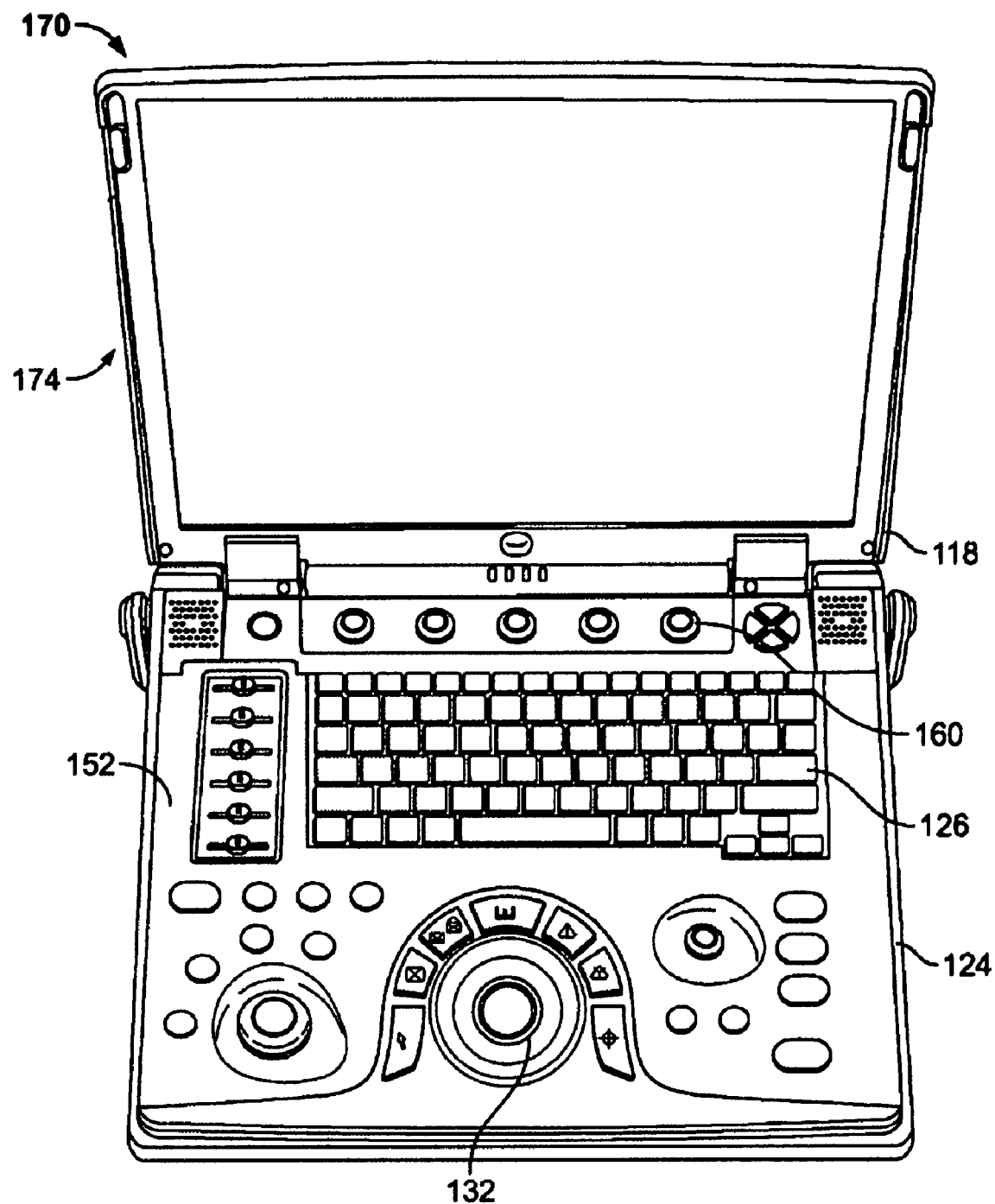
FIG. 5 is a perspective view of a hand carried medical imaging apparatus constructed in accordance with another embodiment of the invention.

Embodiments of the present invention may also be provided in connection with a hand carried imaging apparatus 170 as shown in FIG. 5, wherein display 118 and user interface 124 form a single unit. The hand carried imaging apparatus 170 may be, for example, a handheld or hand carried ultrasound imaging device, such as a miniaturized ultrasound apparatus. As used herein, "miniaturized" means that the ultrasound apparatus is a handheld or hand carried device or is configured to be carried in a person's hand, pocket, briefcase-sized case, or backpack. For example, the hand carried imaging apparatus 170 may be a hand carried device having a size of a typical laptop computer, for instance, having dimensions of approximately 2.5 inches in depth, approximately 14 inches in width, and approximately 12 inches in height. The hand carried imaging apparatus 170 may weigh about ten pounds.

Figure 6:
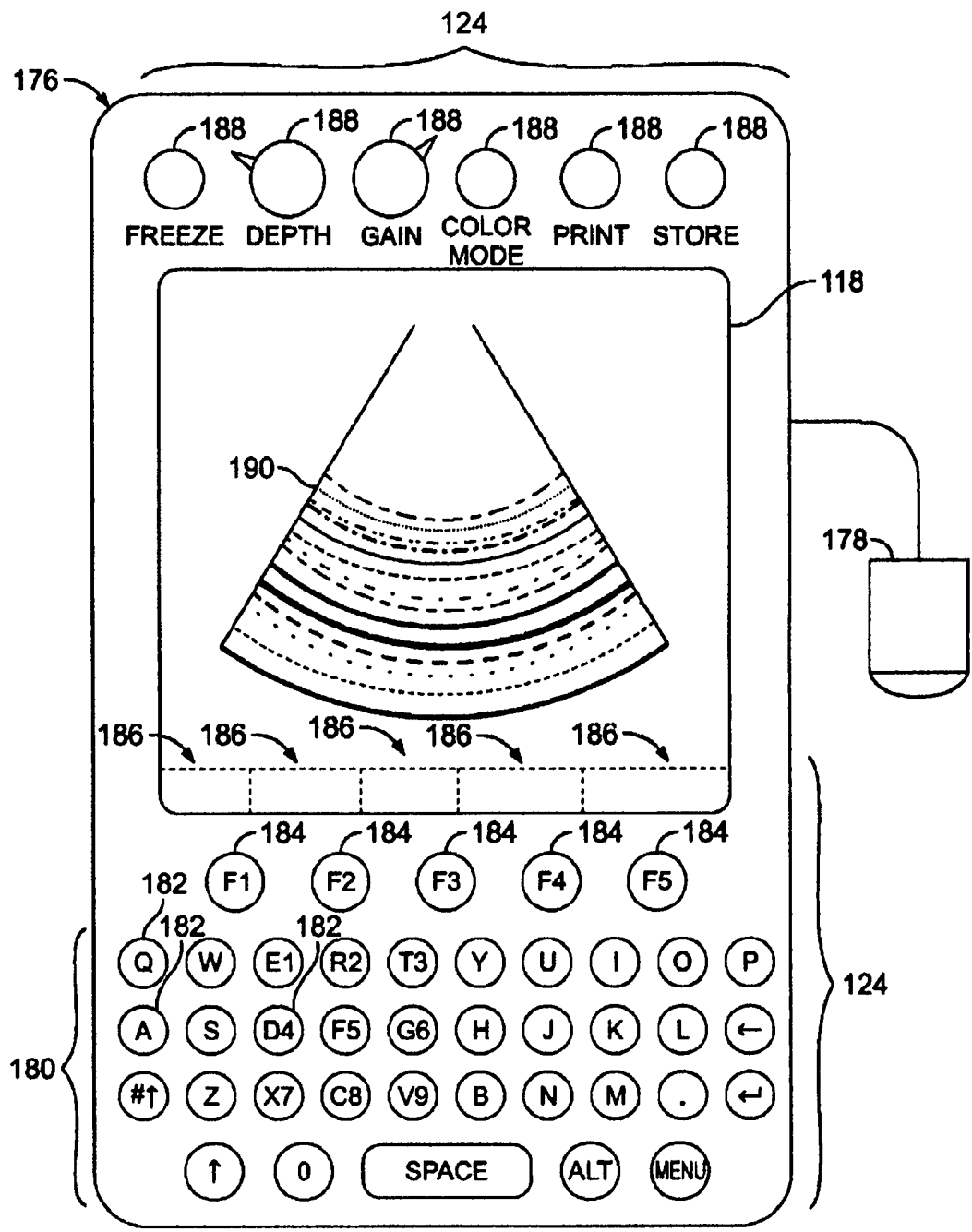
FIG. 6 is a perspective view of a pocket-sized medical imaging apparatus constructed in accordance with another embodiment of the invention.

Embodiments of the present invention may also be provided in connection with a pocket-sized imaging apparatus 176 as shown in FIG. 6, wherein display 118 and user interface 124 form a single hand held unit. By way of example, the pocket-sized imaging apparatus 176 may be a pocket-sized or hand-sized ultrasound apparatus approximately 2 inches wide, approximately 4 inches in length, and approximately 0.5 inches in depth and weigh less than 3 ounces. The pocket-sized imaging apparatus 176 generally includes display 118, user interface 124, which may include a keyboard and an input/output (I/O) port for connection to a scanning device, for example, an ultrasound probe 178. Display 118 may be, for example, a 320×320 pixel color LCD display (on which a medical image 190 may be displayed). A typewriter-like keyboard 180 of buttons 182 may be included in user interface 124. Multi-function controls 184 may each be assigned functions in accordance with the mode of system operation as previously discussed. Label display areas 186 associated with the multi-function controls 184 may be included as necessary on display 118. The device may also have additional keys and/or controls 188 for special purpose functions, which may include, but are not limited to "freeze," "depth control," "gain control," "color-mode," "print," and "store."

The various embodiments may be implemented in connection with miniaturized imaging systems having different dimensions, weights, and power consumption. In some embodiments, the pocket-sized ultrasound apparatus may provide the same functionality as ultrasound imaging apparatus 100 (shown in FIG. 2).

With respect to transmitting pulses, and for example, as described in U.S. Pat. No. 6,494,841, if a transmit pulse is $p(t)=A(t)\cos(\omega t)$, the echo signal for the pulse is $$S(t)=ap(t)+bp(t)^2+cp(t)^3+$$

For a three transmit pulse sequence with the same phase and different amplitudes, for example, amplitudes [0.5, 1, 0.5], and with receive weighting [−1, 1, −1], the combining signal of the three pulses is $$\sum_{i=1}^{3} S(t)_i = 0.5*bp(t)^2 + 0.75*cp(t)^3 + \ldots =$$
$$0.5*bA^2(t)\cos^2(\omega t) + 0.75*cA^3(t)\cos^3(\omega t).$$

The third harmonic signal can be decomposed to $\cos^3(\omega t)=0.75\cos(\omega t)+0.25\cos(3\omega t)$, and the fundamental component, which is called the cubic fundamental signal, can be detected.

In embodiments of the present invention, the transmit amplitude difference is obtained either by adjusting pulse voltage or by adjusting transmit apertures. Embodiments in which the pulse voltage is changed perform best when the pulse amplitude is linear relative to the voltage, so that linear echoes are cancelled out in the combined receive signal.

Figure 7:
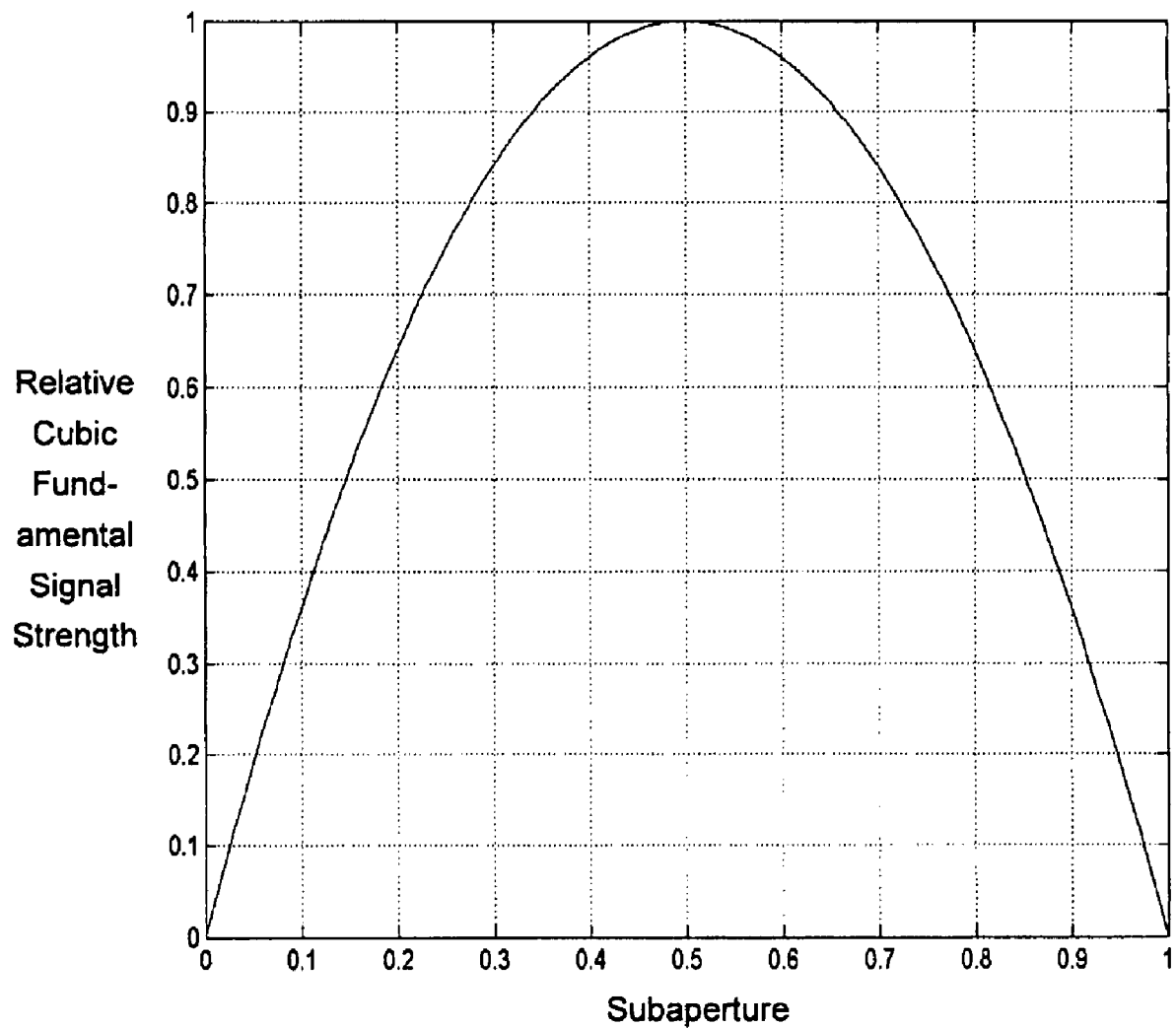
FIG. 7 is a graph showing the relative cubic fundamental strength as a function of the size of a subaperture in one embodiment of the present invention.

Also, embodiments can control the relative amplitude between pulses by adjusting the transmit aperture to achieve different amplitudes. For example, in a three pulse embodiment, one pulse is transmitted with full aperture and two pulses are transmitted with two subapertures, A and B. The sum of the two subapertures A and B equals the full aperture. In one configuration of the present invention, the pulse amplitude is the same for all three pulses for each excited probe element. When the two subapertures are each non-overlapping halves of the full aperture, the transmit amplitude sequence is [0.5, 1, 0.5] and the cubic fundamental signal is the strongest, whereas the linear echoes are cancelled out in the combined receive signal. For a [0.5, 1, 0.5] amplitude sequence, the half subaperture A can be formed by using half of the elements in one side of the aperture, by combining alternative elements, or by any other combination of half the total number of elements in either a regular or a random pattern. Subaperture B is formed using the half of the elements that subaperture A is not using. A similar principle can be used in embodiments having a pulse amplitude sequence of [A, 1, 1−A], where A≠0.5 and A<1, making the first and third amplitudes of the sequence unequal. At a given focus position, if the total number of elements for a full aperture is n (n≦N), the first transmit signal has A*n elements activated, the second transmit signal has all n elements activated and the third transmit signal has all of the elements that are not used in the first transmit signal activated. The three pulses can be transmitted in any order. FIG. 7 is a graph of the cubic fundamental strength for a pulse amplitude sequence of [A, 1, 1−A] as a function of A. When A=0.5, FIG. 7 shows that the cubic fundamental signal is maximized.

Some embodiments of the present invention have a transmit number larger than three. One embodiment of the present invention that uses a transmit sequence larger than three uses a full aperture for one transmit signal and the sum of the subapertures of the rest of the transmit signal equal to the full aperture. Receive weighting for the full aperture is −1 and the weighting for the remainder of the transmit signals is 1, or vice versa. The strongest cubic fundamental signal is obtained when each subaperture uses n/m, m=k−1 elements, where k is the number of transmits. The strength of the third harmonic signal is defined as:

$$\left(-1 + \frac{1}{m^2}\right)*cp^3(t).$$

For example, if the number of the transmit is 5 and each subaperture uses n/4 elements, then the third harmonic strength is $$\frac{15}{16}cp^3(t).$$

Embodiments having a higher number of transmit signals have a stronger cubic fundamental signal and a lower frame rate. In embodiments in which the remainder of n/m is not zero, the subapertures can comprise a number of elements equal to int(n/m) or int(n/m+1), provided that the sum of the subapertures is equal to the full aperture.

Figure 8:
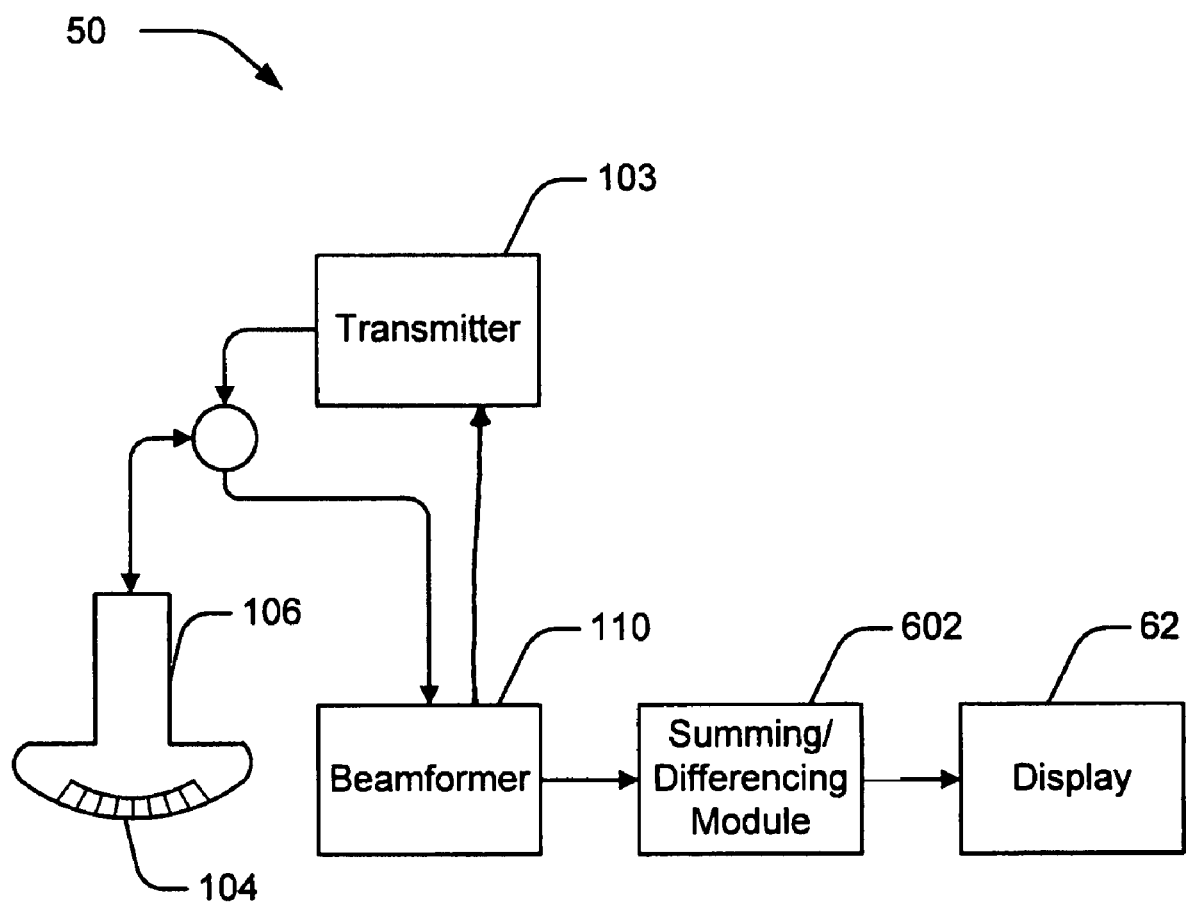
FIG. 8 is a schematic block diagram representative of some apparatus embodiments of the present invention.
Figure 9:
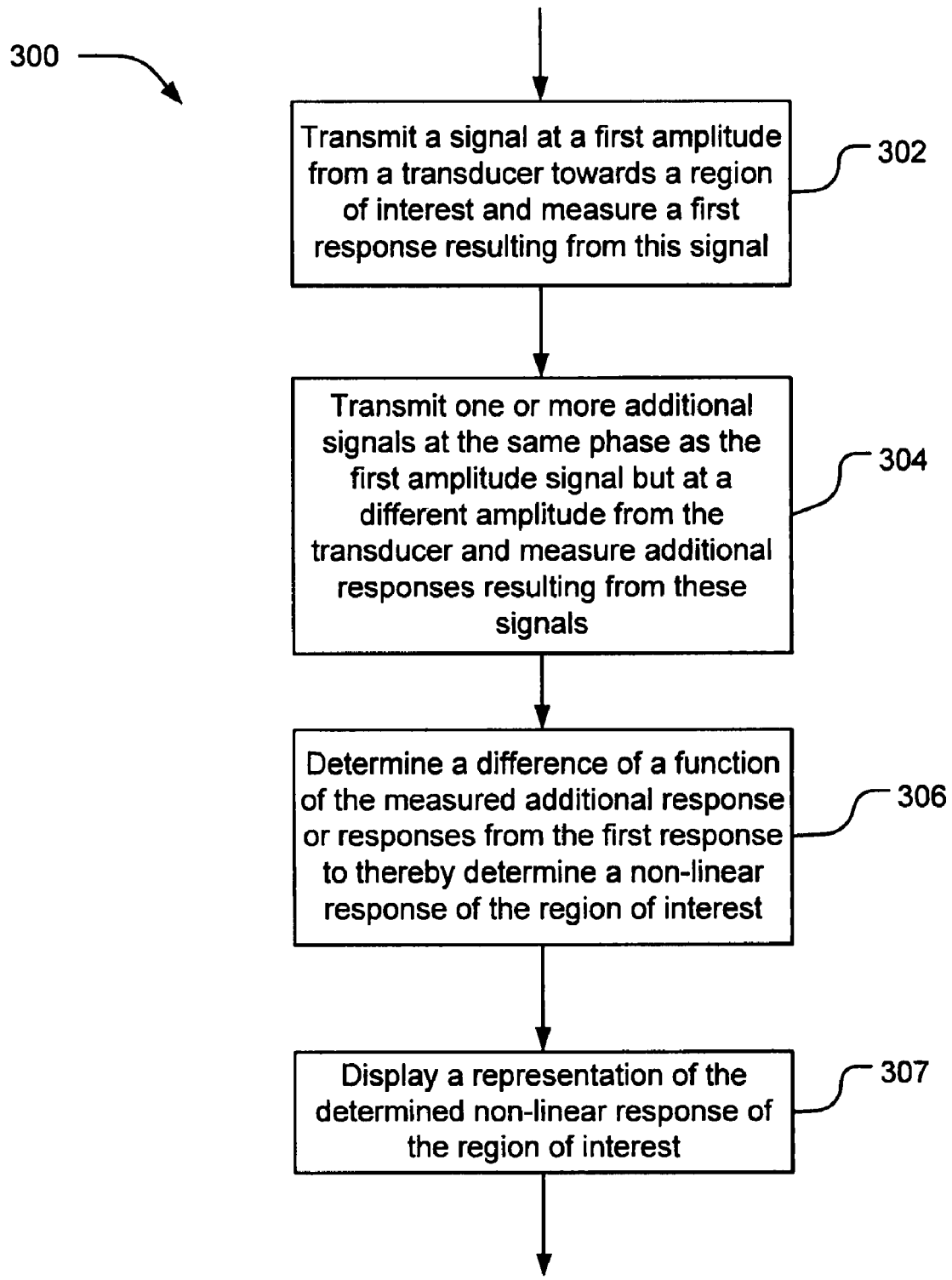
FIG. 9 is a flow chart illustrating a method for measuring a non-linear response from a target in accordance with an embodiment of the invention.

A technical effect of at least one embodiment of the present invention is to measure and/or display a non-linear response from a target, such as a contrast agent and a tissue, to provide an indication of an anomalous condition, such as a disease, with multiple transmit pulses that do not require phase shifting and exact symmetry. FIG. 8 is a schematic block diagram of an embodiment 50 of the present invention configured to provide this technical effect by measuring a non-linear response from a target (which may comprise a contrast agent). FIG. 9 is a flow chart 300 of a method embodiment that uses an imaging apparatus 50 of the type shown in FIG. 8. Referring to FIGS. 8 and 9, imaging apparatus 50 includes a transmitter 102, a transducer 106 having a plurality N of excitable transducer elements 104 excitable by transmitter 102, a beamformer 110 configured to receive echo return signals from transducer elements 104, a summing/differencing module 602 configured to determine a non-linear response, and a display 62 configured to display a representation of the determined non-linear response. The method illustrated by flow chart 300 includes, at 302, transmitting a signal at a first amplitude towards a region of interest from transducer 106 and measuring a first response thereto (e.g., utilizing beamformer 110). At 304, one or more additional signals are transmitted at the same phase from transducer 106 towards the region of interest as the first amplitude signal but at a different amplitude from the transducer, and one or more additional responses are measured, corresponding to each additional signal. The first amplitude signal and the additional signal or signals need not be transmitted in any particular order, as long as the order is known. The method also includes, at 306, determining a difference (using summing/differencing module 602) of a function of the measured additional response or responses from the first response to thereby determine a non-linear response of the region of interest. The method further includes, at 307, displaying a representation of the non-linear response on display 62. In some embodiments of the present invention, the non-linear response is a cubic fundamental response.

Figure 10:
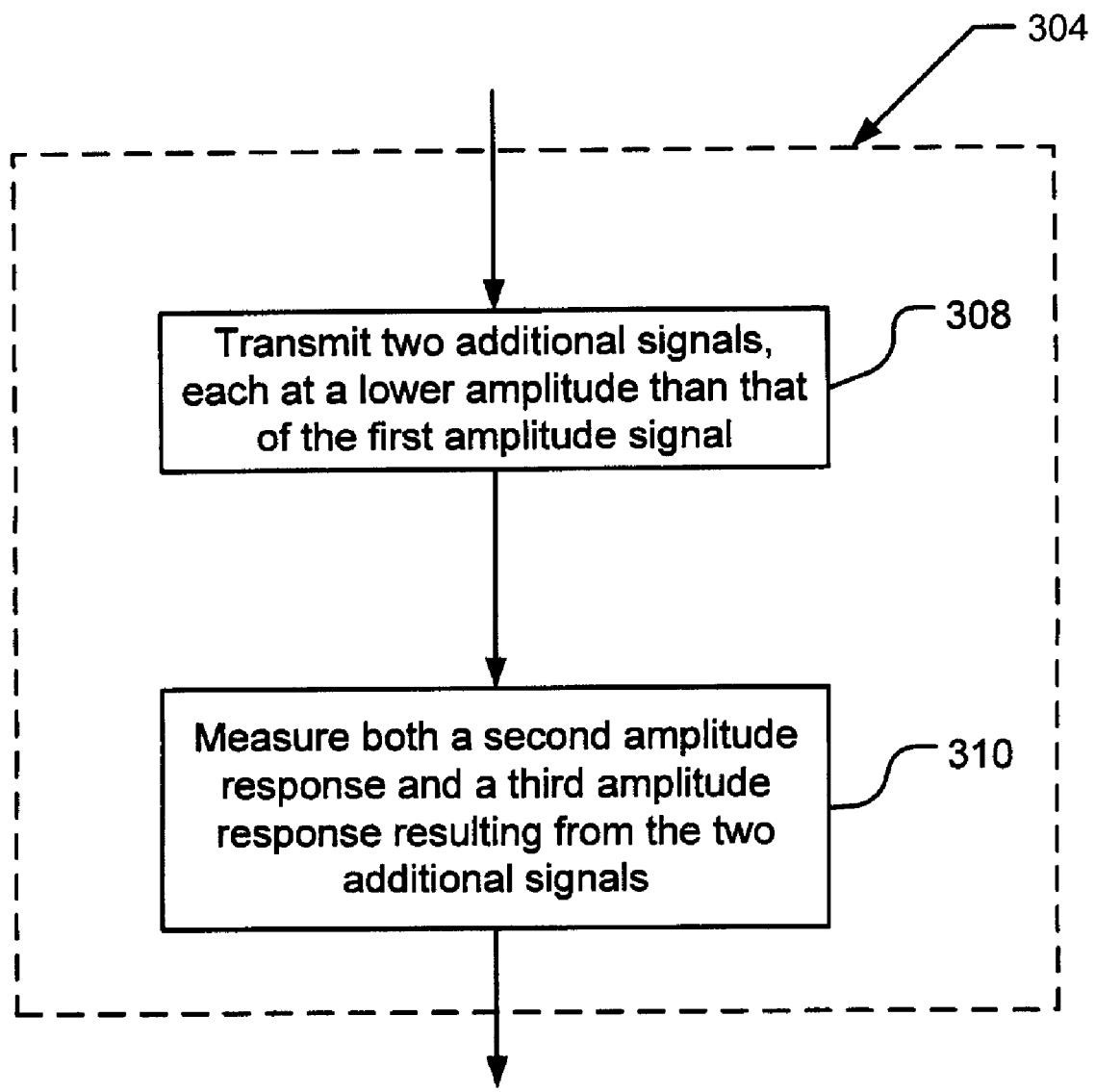
FIG. 10 is a flow chart detailing one of the blocks shown in the flow chart in FIG. 9 for some embodiments of the present invention.

FIG. 10 is a flow chart showing details of block 304 in some embodiments of the present invention. At 308, two additional signals are transmitted at a lower amplitude than that of the first amplitude signal, and at 310, both a second amplitude response and a third amplitude response are measured. In at least one embodiment, the amplitudes of the two additional signals are selected to maximize the cubic fundamental response in the determined non-linear response. However, the amplitudes of the two additional signals are not required to be the same in all configurations of the present invention.

Figure 11:
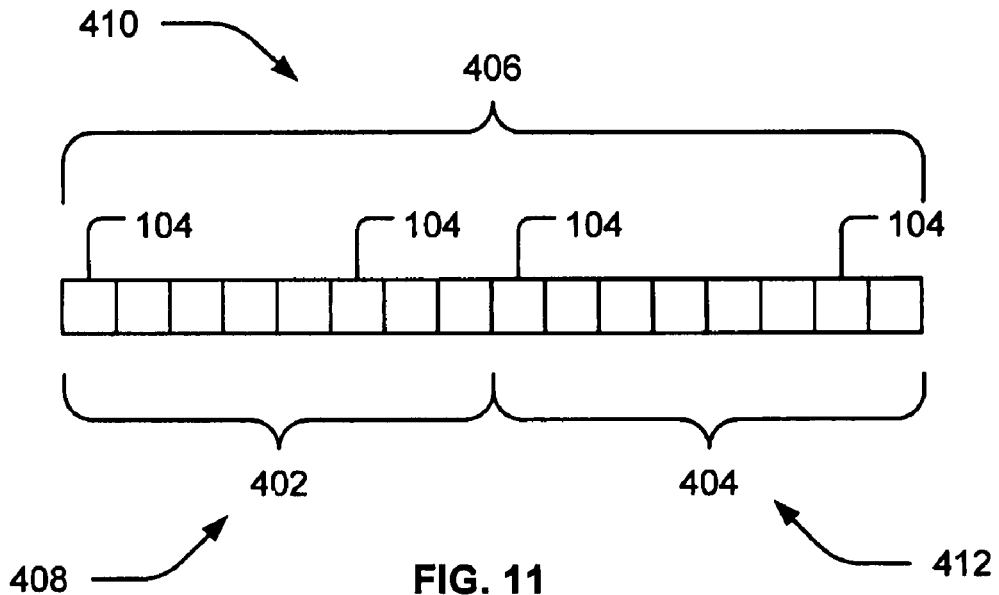
FIG. 11 is a drawing illustrating a selection of subapertures of some embodiments of the present invention.
Figure 12:
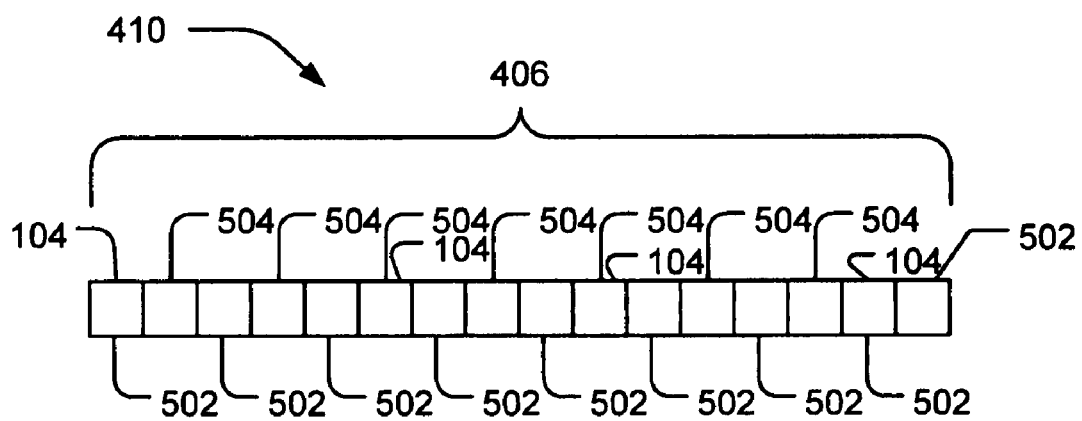
FIG. 12 is a drawing illustrating a selection of subapertures of some other embodiments of the present invention.

FIGS. 11 and 12 are drawings illustrating selections of subapertures for some embodiments of the present invention. In these embodiments, block 302 further comprises transmitting a signal towards a region of interest using a first aperture 406 of elements of transducer 106 and block 304 further comprises transmitting at least one additional signal towards the region of interest using at least one subaperture (e.g., 402 or 502) of first aperture 406. In many of these embodiments, the "at least one additional signal" comprises two additional signals that are complementary subapertures (e.g., 402 and 404, or 502 and 504) of first aperture 406. By "complementary subapertures," it is meant that the sum of the complementary apertures equals the full aperture. For example, a subaperture can be selected by exciting with transmitter 102 only those elements 104 that belong to that subaperture, or by physically blocking the transmission of a signal from elements 104 outside of that subaperture in embodiments in which it is feasible to do so. Block 306 further comprises determining a difference between the first response and a function of the sum of the additional responses. In some embodiments, the amplitudes of each of the two additional signals (i.e., the second signal and the third signal) are equal to one-half of the first amplitude, so that determining a difference between the first response and a function of the sum of the additional responses at block 306 is simply a matter of determining a difference between the first response and the sum of the additional responses.

It is convenient in some embodiments to utilize subapertures 402 and 404 for the second and third transmitted signal that comprise exactly half of the elements 104 of the entire set 410 of elements 104 of transducer 106 on opposite sides 408 and 412 of aperture 406, as shown in FIG. 11. Subaperture 402 thus is located on one side 408 of aperture 406, and subaperture 404 is located on the other side 412 of aperture 406.

In some other embodiments, and as shown by elements 502 and 504 in FIG. 12, it is convenient for the subapertures for the second and third transmitted signal to comprise interleaved halves of the full set 410 of elements 104 of transducer 106.

Although the arrangements of subapertures illustrated in FIGS. 11 and 12 are convenient, other arrangements, including pseudo-random arrangements and any patterned half arrangement can be used in other embodiments of the present invention.

The physical size of embodiments of the present invention can vary from a full-size imaging apparatus to a pocket-size imaging apparatus. For example, in some embodiments of the present invention, the imaging apparatus is an ultrasound imaging apparatus 100. Ultrasound imaging apparatus may be a miniaturized apparatus, for example, a hand carried imaging apparatus 170 or a pocket-sized imaging apparatus 176.

In yet another embodiment of the present invention, rather than using different apertures, each of the elements 104 of transducer 106 are excited more than once, but transmitter 102 provides pulses at differing amplitudes for each pulse. More particularly, block 302 comprises exciting a set of transducer elements 104, and block 304 comprises exciting the same set of transducer elements 104 at (one or more) different, lesser amplitude(s). Furthermore, block 306 comprises weighting the additional response or responses by the ratio of the first amplitude to (each corresponding) different, lesser amplitude. For example, for a sequence with two transmits, if the second transmit amplitude is 1/m relative to the amplitude of the first transmit, then the receiving weighting is [1, −m] for the first and the second received signals, respectively.

Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

It will thus be appreciated that embodiments of the present invention provide methods and apparatus that impose no requirement on pulse symmetry and allow the use of inexpensive components in ultrasound imaging systems.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for measuring a non-linear response from a target using an imaging apparatus, said apparatus comprising a transmitter, a transducer having a plurality N of excitable transducer elements excitable by the transmitter, a beamformer configured to control a focus for transmit and receive signals from the transducer elements, a summing/differencing module responsive to the beamformer and configured to determine a non-linear response, and a display configured to display a representation of the determined non-linear response;

said method comprising:

transmitting a signal towards a region of interest from the transducer at a first amplitude and measuring a first response thereto;

transmitting, from the transducer towards the region of interest, at least one additional signal of the same phase as the first amplitude signal and at one or more different, lower amplitudes, and measuring at least one additional response thereto, wherein the at least one additional signal is transmitted using a random arrangement of subaperture transducer elements;

determining a difference of a function of said measured at least one additional response from the first response to determine a non-linear response of the object of interest; and displaying a representation of the non-linear response on the display.

2. A method in accordance with claim 1 wherein the non-linear response is a cubic fundamental response.

3. A method in accordance with claim 2 wherein said at least a one additional response comprises a second response and a third response, and the lower amplitudes are selected to maximize the cubic fundamental response.

4. A method in accordance with claim 1 wherein said transmitting a signal towards a region of interest further comprises transmitting a signal towards a region of interest using a first aperture of elements of the transducer and said transmitting at least one additional signal further comprises transmitting at least one additional signal towards the region of interest using at least one subaperture set of the first aperture.

5. A method in accordance with claim 4 wherein said at least one additional signal comprises two additional signals from complementary subapertures of the first aperture, and said determining a difference comprises determining a difference between the first response and a function of the sum of the additional responses.

6. A method in accordance with claim 5 wherein the amplitudes of each of the two additional signals is equal to one-half of the first amplitude and said determining a difference between the first response and a function of the sum of the additional responses comprises determining a difference between the first response and the sum of the additional responses.

7. A method in accordance with claim 6 wherein the subapertures comprise half of the elements of the transducer on opposite sides of the transducer.

8. A method in accordance with claim 6 wherein the subapertures comprise one of interleaved halves of the elements of the transducer, random halves of the elements of the transducers and patterned halves of the elements of the transducer.

9. A method in accordance with claim 4 wherein the imaging apparatus is an ultrasound imaging apparatus.

10. A method in accordance with claim 4 wherein the imaging apparatus is a hand-carried or pocket-sized ultrasound imaging apparatus.

11. A method in accordance with claim 1 wherein said transmitting a signal towards a region of interest from the transducer at a first amplitude comprises exciting a set of transducer elements and said transmitting at least one additional signal of the same phase as the first amplitude signal but at a different amplitude comprises exciting the same set of transducer elements at a different, lesser amplitude, and said determining a difference of a function of said measured at least one additional response from the first response further comprises weighting said at least one additional response by the ratio of the first amplitude to the different, lesser amplitude.

12. A diagnostic imaging apparatus for measuring a non-linear response from a target,
said apparatus comprising:
a transmitter;
a transducer having a plurality N of excitable transducer elements excitable by the transmitter;
a beamformer configured to focus a beam from the transducer at a position to transmit acoustic energy and to receive echo return signals from the transducer elements;
a summing/differencing module configured to determine a non-linear response; and
a display configured to display a representation of the determined non-linear response;
said apparatus configured to:
transmit a signal towards a region of interest from the transducer at a first amplitude and measure a first response thereto;
transmit, from the transducer towards the region of interest, at least one additional signal of the same phase as the first amplitude signal and at one or more lesser amplitudes, and measure at least one additional response thereto, wherein the at least one additional signal is transmitted using a random arrangement of subaperture transducer elements;
determine a difference of a function of said measured at least one additional response from the first response to thereby determine a non-linear response of the object of interest; and
display a representation of the non-linear response on the display.

13. An apparatus in accordance with claim 12 wherein the non-linear response is a cubic fundamental response.

14. An apparatus in accordance with claim 13 wherein said at least one additional response comprises a second response and a third response, and the lesser amplitudes are selected to maximize the cubic fundamental response in the determined non-linear response.

15. An apparatus in accordance with claim 12 wherein to transmit a signal towards a region of interest, said apparatus is further configured to transmit a signal towards a region of interest using a first aperture of elements of the transducer, and to transmit said at least one additional signal, said apparatus is further configured to transmit at least one additional signal towards the region of interest using at least one subaperture of the first aperture.

16. An apparatus in accordance with claim 15 wherein said at least one additional signal comprises two additional signals of complementary subapertures of the first aperture, and to determine said non-linear response of the object of interest, said apparatus is configured to determine a difference between the first response and a function of the sum of the additional responses.

17. An apparatus in accordance with claim 16 wherein the amplitudes of each of the two additional signals is equal to one-half of the first amplitude, and to determine a difference between the first response and a function of the sum of the additional responses, said apparatus is configured to determine a difference between the first response and the sum of the additional responses.

18. An apparatus in accordance with claim 12 wherein to transmit a signal towards a region of interest, said apparatus is configured to excite a set of transducer elements at a first amplitude, and to transmit at least one additional signal, said apparatus is configured to excite the same set of transducer elements at a different, lesser amplitude, and to determine a difference of a function of said measured at least one additional response from the first response, said apparatus is further configured to weight said at least one additional response by the ratio of the first amplitude to the different, lesser amplitude.

19. An ultrasound imaging apparatus comprising:
a transmitter;
a transducer having a plurality N of excitable transducer elements excitable by the transmitter;
a beamformer configured to control focus for transmit and receive signals from the transducer elements;
a summing/differencing module responsive to the beamformer and configured to determine a non-linear response utilizing signals received from the transducer elements; and
a display configured to display an image utilizing the determined non-linear response;
and said apparatus is configured to:
transmit a signal towards a region of interest from the transducer at a first amplitude and measure a first response thereto;
transmit, from the transducer towards the region of interest, at least one additional signal of the same phase as the first amplitude signal and at a different amplitude, and measuring at least one additional response thereto, wherein the at least one additional signal is transmitted using a random arrangement of subaperture transducer elements;
determine a difference of a function of said measured at least one additional response from the first response to determine a non-linear response of the object of interest; and
display a representation of the non-linear response on the display.

20. An apparatus in accordance with claim 19 wherein the apparatus is a hand-carried or pocket-sized ultrasound imaging apparatus.

* * * * *